United States Patent [19]
Uchida et al.

[11] Patent Number: 4,464,244
[45] Date of Patent: Aug. 7, 1984

[54] OXYGEN SENSING DEVICE HAVING SOLID ELECTROLYTE CELL AND MEANS FOR SUPPLYING CONTROLLED CURRENT THERETO

[75] Inventors: Masaaki Uchida; Shigeo Isitani, both of Yokosuka, Japan

[73] Assignee: Nissan Motor Company, Limited, Yokohama, Japan

[21] Appl. No.: 386,427

[22] Filed: Jun. 8, 1982

[30] Foreign Application Priority Data

Jun. 23, 1981 [JP] Japan .................. 56-97235

[51] Int. Cl.$^3$ ............................. G01N 27/46
[52] U.S. Cl. ................... 204/425; 204/1 T; 204/424; 204/426; 204/429
[58] Field of Search ........... 204/1 S, 195 S, 421, 204/424–429

[56] References Cited

U.S. PATENT DOCUMENTS

| | | | |
|---|---|---|---|
| 3,616,274 | 10/1971 | Eddy | 204/195 S |
| 4,135,381 | 1/1979 | Sherwin | 204/195 S |
| 4,207,159 | 6/1980 | Kimura et al. | 204/195 S |
| 4,224,113 | 9/1980 | Kimura et al. | 204/195 S |
| 4,332,225 | 6/1982 | Cox et al. | 204/195 S |
| 4,359,030 | 11/1982 | Sone et al. | 204/195 S |

FOREIGN PATENT DOCUMENTS 2060177 4/1981 United Kingdom .

Primary Examiner—T. Tung
Attorney, Agent, or Firm—Jeffery, Schwaab, Mack, Blumenthal & Koch Schwartz

[57] ABSTRACT

A device for detecting concentrations of oxygen in gases by using an oxygen sensor element having a substrate provided with a heater and a concentration cell part in the form of a laminate including a solid electrolyte layer supported on the substrate. The device has a power supply circuit to apply a controlled voltage to the heater to keep it at a constant temperature by controlling its resistance to a constant value, and a current supply circuit which forces a controlled DC current to flow through the solid electrolyte layer in the sensor element to thereby maintain a reference oxygen partial pressure in the sensor element. The current supply circuit is electrically associated with the power supply circuit so as to vary the intensity of the current in inverse proportion to the voltage applied to the heater for the purpose of maintaining the reference oxygen partial presure constant even when the temperature of the concentration cell part of the sensor element varies depending on the temperature of the gas subject to measurement.

5 Claims, 9 Drawing Figures

OXYGEN SENSING DEVICE HAVING SOLID ELECTROLYTE CELL AND MEANS FOR SUPPLYING CONTROLLED CURRENT THERETO

BACKGROUND OF THE INVENTION

This invention relates to a device for detecting concentrations of oxygen in gases, the device being of the type having an oxygen sensor element of the concentration cell type using an oxygen ion conductive solid electrolyte and having a heater, a power supply circuit to apply a controlled voltage to the heater and a current supply circuit to supply a controlled current to the sensor element in order to maintain a reference oxygen partial pressure in the sensor element.

Recently oxygen sensors have been largely applied to automobiles for the purpose of detecting concentrations of oxygen in exhaust gases discharged from the automotive engines as the basis for electronic feedback control of air/fuel ratio of the gas mixture supplied to the engines. Usually oxygen sensors for this purpose are of the concentration cell type having a layer of an oxygen ion conductive solid electrolyte such as zirconia containing a small amount of a stabilizing oxide. In an oxygen sensor of this type is is necessary to maintain a reference partial pressure of oxygen on one side of the solid electrolyte layer.

In this field, a recent trend is to miniaturize the oxygen-sensitive element of the sensor by constructing it as a laminate of thin, film-like layers on a plate-shaped ceramic substrate of very small size. As described in U.S. Pat. No. 4,224,113, a reference oxygen partial pressure of a nearly constant level can be maintained in this sensor element by supplying a DC current of the order of $10^{-6}$ to $10^{-5}$ A to the concentration cell part of the sensor element so as to flow through the solid electrolyte layer thereby controlling the migration of oxygen ions in the solid electrolyte layer. Since the solid electrolyte does not exhibit its proper function at temperatures below a certain level such as about 400° C., the substrate of the oxygen sensor element is provided with a heater to which an adequate voltage is applied for the purpose of maintaining the sensor element at a nearly constant temperature. However, the temperature of the concentration cell part of the sensor element varies considerably depending on the temperatures of the gases subject to measurement with resultant changes in the level of the reference oxygen partial pressure in the sensor element and in the output characteristic of the sensor element.

In operating the above described oxygen sensor element in automotive engine exhaust gases which undergo frequent changes in the temperature thereof over a very wide range, it becomes a matter of importance to the achievement of accurate detection of oxygen concentrations in the exhaust gases and high-precision control of air/fuel ratio to prevent changes in the level of the reference oxygen partial pressure in the sensor element with variations in the exhaust gas temperature.

SUMMARY OF THE INVENTION

It is an object of the present invention to provide an improved device for detecting concentrations of oxygen in gases, the device being a combination of an oxygen sensor element of the concentration cell type using an oxygen ion conductive solid electrolyte and having heater, a power supply circuit to supply a controlled DC current to the sensor element in order to maintain a reference oxygen partial pressure in the sensor element, and the device being capable of controlling the intensity of said current so as to keep the reference oxygen partial pressure at a constant level even when the temperature of the concentration cell part of the sensor element varies depending on the temperature of gases subject to measurement.

A device according to the invention includes an oxygen sensor element which has a ceramic substrate provided with a heater and a laminate of a reference electrode layer, an oxygen ion conductive solid electrolyte layer and a measurement electrode layer supported on the substrate, a power supplying means for applying a controlled voltage to the heater in the sensor element so as to maintain the heater at a predetermined temperature by controlling the resistance of the heater to a constant value, and a current supplying means for supplying a controlled DC current to the sensor element such that the current flows in the solid electrolyte layer from the reference electrode layer toward the measurement electrode layer to cause oxygen ions to migrate in the solid electrolyte layer from the measurement electrode layer toward the reference electrode layer to thereby maintain a reference oxygen partial pressure at the interface between the reference electrode layer and the solid electrolyte layer. As the improvement according to the invention, this device comprises a link means for electrically associating the current supplying means with the power supplying means to transmit a voltage signal representative of the voltage applied to the heater to the current supplying means, and the current supplying means is made to have the function of varying the intensity of the current being supplied to the sensor element in inverse proportion to the magnitude of the voltage applied to the heater.

The control of the intensity of the current being supplied to the sensor element in the above stated correlation with the voltage applied to the heater results in that the concentration cell part of the sensor element is supplied with an increasing current as the temperature of this part rises even though the heater in the substrate is maintained at a constant temperature. Therefore, the reference oxygen partial pressure in the sensor element remains at a constant level without being influenced by the temperature of the gases subject to measurement such as exhaust gases of automotive engines, so that the output characteristic of the sensor element is scarcely influenced by the temperature of the gases. By using a device according to the invention in the exhaust system of an internal combustion engine, it is possible to accomplish electronic feedback control of air/fuel ratio of a gas mixture supplied to the engine with a considerably improved precision.

DESCRIPTION OF THE PREFERRED EMBODIMENT

Figure 1:
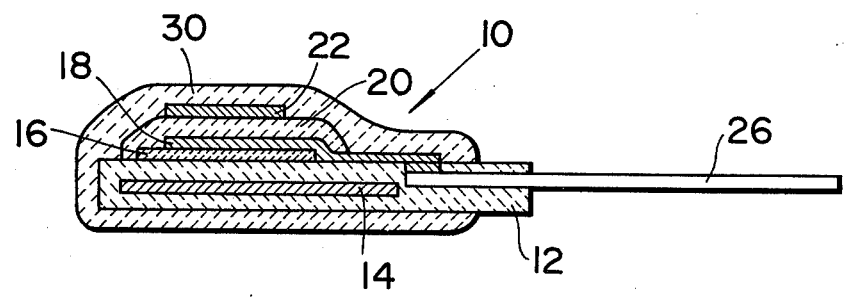
FIG. 1 is an explanatorily sectional view of an oxygen sensor element.
Figure 2:
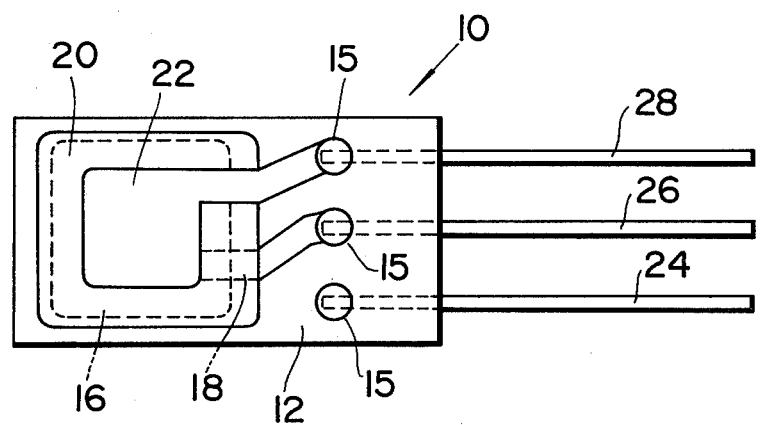
FIG. 2 is an explanatory plan view of the oxygen sensor element of FIG. 1.

FIGS. 1 and 2 show a known oxygen sensor element 10 which is to be operated by using a current control device according to the invention. A structurally basic member of this element 10 is a plate-shaped substrate 12 made of an electrically insulating ceramic material such as alumina. A heater 14 (omitted from illustration in FIG. 2) in the form of either a thin film-like layer or a thin wire of a suitable metal such as platinum is embedded in the substrate 12. It is a usual practice to prepare the substrate 12 by face-to-face bonding of two ceramic sheets one of which is precedingly provided with the heater 14.

The sensitive part of this oxygen sensor element 10 takes the form of a laminate of thin layers supported on the ceramic substrate 12. The laminate includes an intermediate layer 16 formed on a major surface of the substrate 12 so as to cover a sufficiently large area of the substrate surface. This intermediate layer 16 is formed of a ceramic material. An inner electrode layer 18, which is often called reference electrode layer, lies on the upper surface of the intermediate layer 16 so as to leave a marginal region of the surface of the intermediate layer 16 uncovered. Platinum is a typical material for this electrode layer 18. A layer 20 of an oxygen ion conductive solid electrolyte such as $ZrO_2$ containing a small amount of a stabilizing oxide such as $Y_2O_3$ or CaO closely covers the upper surface of the inner electrode layer 18 and comes into direct contact with the marginal region of the intermediate layer 16, so that the inner electrode layer 18 is substantially entirely enclosed by the intermediate layer 16 and the solid electrolyte layer 20. This solid electrolyte layer 20 has a microscopically porous structure. An outer electrode layer 22, which is usually formed of platinum and often called measurement electrode layer, lies on the upper surface of the solid electrolyte layer 20. The thus constructed laminate has a total thickness of about 70 microns for example, and each layer of this laminate can be formed by utilizing a so-called thick-film technique.

This oxygen sensor element 10 has three lead wires 24, 26, 28, usually of platinum, which are inserted into the substrate 12 in their tip portions. The first lead wire 24 is connected to one terminal of the heater 14 within the substrate 12. The second lead wire 26 is connected to the inner electrode layer 18 by using one of holes 15 formed in the upper half of the substrate 12 and a conductor filled in the hole 15. In a similar manner, the third lead wire 28 is connected to the outer electrode layer 22, and this lead wire 28 is connected also to the other terminal of the heater 14.

As is known, the solid electrolyte layer 20 and the two electrode layers 18 and 22 constitute an oxygen concentration cell that generates an electromotive force when there is a difference between a partial pressure of oxygen on the outer electrode side of the solid electrolyte layer 20 and an oxygen partial pressure on the inner electrode side of the same layer 20. The intermediate layer 16 is not essential to the oxygen concentration cell, but this layer 16 is added for the purpose of enhancing the strength of adhesion of the laminated oxygen concentration cell to the ceramic substrate 12. Preferably, the intermediate layer 16 is formed of the same solid electrolyte material as the one used for the layer 20.

The outer surfaces of the laminated sensitive part of this sensor element 10 and a major part of the substrate 12 are covered with a porous protecting layer 30 formed of a ceramic material such as spinel (in FIG. 2, the protecting layer 30 is omitted from illustration for simplicity), so that a gas subject to measurement comes into contact with the outer electrode layer 22 through the micropores in this protecting layer 30.

Figure 3:
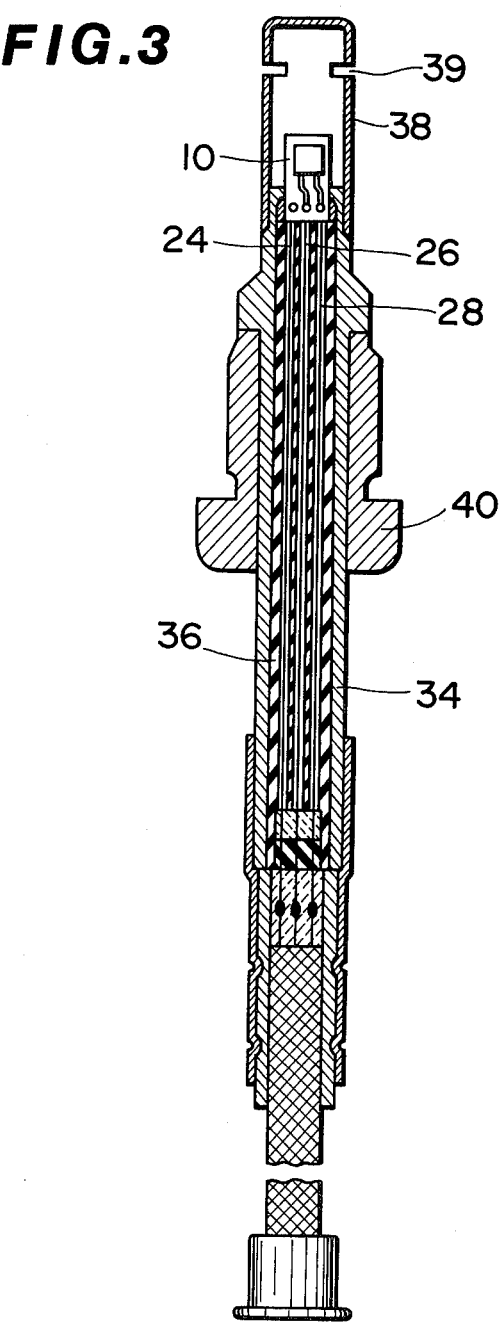
FIG. 3 is a longitudinal sectional view of an oxygen sensor which includes the sensor element of FIGS. 1 and 2 and is so designed as to be useful in the exhaust system of an automotive engine.

FIG. 3 shows an exemplary construction of an oxygen sensor which utilizes the sensor element 10 of FIG. 1 and is designed for attachment to the exhaust pipes or exhaust manifolds of automotive internal combustion engines. This sensor has a tubular case 34 of stainless steel, and a rod 36 of an insulating ceramic material such as mullite is tightly fitted into the case 34. The oxygen sensor element 10 of FIG. 1 is fixedly mounted on a forward end of the ceramic rod 36, and the three lead wires 24, 26, 28 of the sensor element 10 are extended respectively through three axial holes (no numeral) bored in the ceramic rod 36. A cup-shaped hood 38 of stainless steel is fixed to the forward end of the tubular case 34 so as to enclose the sensor element 10 therein. The side wall of the hood 38 is formed with apertures 39 to admit the exhaust gas into the interior of the hood 38, so that the oxygen sensor element 10 can be exposed to the exhaust gas. To insert only the hooded end portion of the sensor into the exhaust pipe and fix the sensor to a boss provided to the exhaust pipe, a threaded metal body 40 is fitted around the tubular case 34 in a region close to the hood 38.

To detect the concentration of oxygen in the exhaust gas by using this oxygen sensor to thereby detect the air/fuel ratio of an air-fuel mixture actually supplied to the engine, it is necessary to produce and maintain a nearly constant partial pressure of oxygen at the interface between the inner electrode layer 18 and the solid electrolyte layer 20 in the oxygen sensor element 10. For this purpose, a DC current is supplied from an external power source to the sensor element 10 by using the second and third lead wires 26 and 28 such that the current flows in the solid electrolyte layer 20 from the inner electrode layer 18 toward the outer electrode layer 22. Besides, a suitable voltage is applied to the heater 14 from a separate power source by using the first and third lead wires 24 and 28. Thus, the third lead wire 28 serves as a grounding lead common to the oxygen concentration cell in the sensor element 10 and the heater 14. To measure an electromotive force the sensor element 10 generates, a potentiometer or an alternative instrument is connected between the inner and outer electrode layers 18 and 22, i.e. between the second and third lead wires 26 and 28.

The flow of the DC current in the solid electrolyte layer 20 causes oxygen ions to migrate through the solid electrolyte layer 20 from the outer electrode layer 22 toward the inner electrode layer 18, and an increasing quantity of oxygen ions migrate in this way as the intensity of the DC current is augmented. The oxygen ions arriving at the inner electrode layer 18 are converted to oxygen molecules, which gradually diffuse outwardly through the micropores in the solid electrolyte layer 20. Consequentially an oxygen partial pressure of a nearly constant magnitude determined by a balance between the inflow of oxygen ions and the outflow of oxygen molecules is maintained at the interface between the inner electrode layer 18 and the solid electrolyte layer 20. The source of the oxygen ions migrating from the outer electrode layer 22 toward the inner electrode layer 18 is oxygen molecules diffused through the porous protecting layer 30 from the ambient gas atmosphere subject to measurement toward the outer electrode layer 22. Accordingly the level of an oxygen partial pressure at the outer electrode layer 22 is determined by the proportion of the oxygen ion migrating toward the inner electrode 18 to the oxygen molecules supplied to the outer electrode layer 22 through the porous protecting layer 30. By appropriately determining the intensity of the DC current flowing in the solid electrolyte 20, it is possible to make the oxygen partial pressure $P_1$ at the inner electrode layer 18 higher than the oxygen partial pressure $P_2$ at the outer electrode layer 22. Under these conditions, the oxygen sensor element 10 generates an electromotive force E according to the Nernst's equation $$E = (RT/4F)\ln(P_1/P_2)$$

where R is the gas constant, F is the Faraday constant, and T represents the absolute temperature.

Since the oxygen partial pressure $P_2$ at the outer electrode layer 22 is approximately proportional to the partial pressure or concentration of oxygen in the gas subject to measurement, the magnitude of the electromotive force E depends on the concentration of oxygen in the gas subject to measurement so long as the temperature of the concentration cell part of the oxygen sensor element 10 and the intensity of the DC current flowing in the solid electrolyte layer 20 remain unchanged and lowers as the oxygen concentration in the gas becomes higher. During operation of the oxygen sensor element 10, a controlled voltage is applied to the heater 14 in the substrate 12 so as to maintain the concentration cell part of the sensor element 10 at a practically constant temperature.

Figure 4:
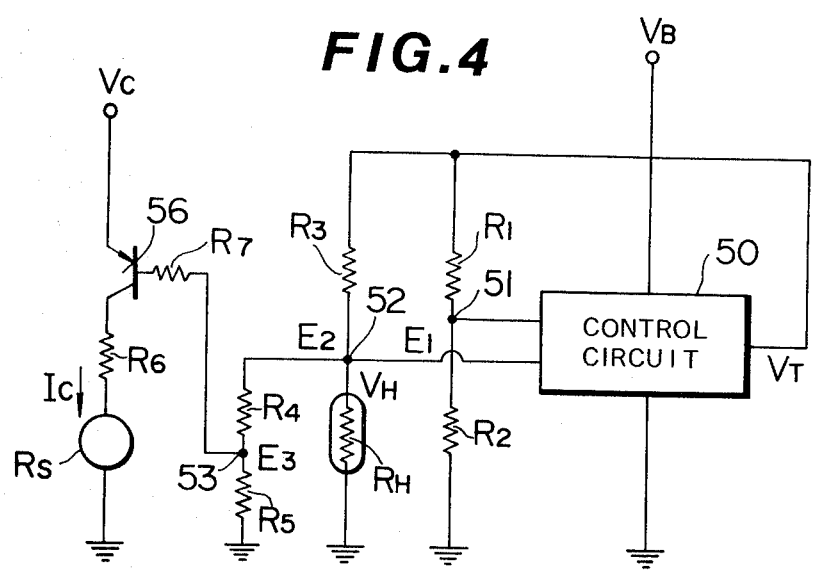
FIG. 4 is a circuit diagram showing a device embodying the present invention for operating the oxygen sensor element of FIG. 1.

FIG. 4 shows a device which embodies the present invention and includes the oxygen sensor element of FIG. 1. In the circuit diagram of FIG. 4, reference character $R_S$ represents the concentration cell part of the oxygen sensor element 10, i.e. the solid electrolyte layer 20 sandwiched between the outer and inner electrode layers 22 and 18, and $R_H$ represents the resistance of the heater 14 embedded in the substrate 12 of the sensor element 10.

To apply a controlled voltage to the heater $R_H$ so as to maintain the heater at a predetermined temperature by using a fixed voltage $V_B$ such as the output voltage of a battery, the device of FIG. 4 has a voltage modulating circuit 50 and three fixed resistances $R_1$, $R_2$ and $R_3$. The resistance $R_3$ is connected in series with the heater resistance $R_H$, and the resistances $R_1$ and $R_2$ are connected in series with each other and parallel to the resistances $R_3$ and $R_H$. These four resistances $R_1$, $R_2$, $R_3$ and $R_H$ constitute a bridge network as can be seen, and the resistance values thereof are determined such that the following relation holds: $R_3 < R_H < < R_1 < R_2$. A potential $E_1$ at the bridge point 51 between the resistances $R_1$ and $R_2$ and another potential $E_2$ at the bridge point 52 between the resistance $R_3$ and the heater resistance $R_H$ are put into the voltage modulating circuit 50. When the bridge network is applied with a voltage $V_T$ produced by the voltage modulating circuit 50, the potential $E_1$ and $E_2$ are given respectively by the following equations.

$$E_1 = (V_T \cdot R_2)/(R_1 + R_2)$$

$$E_2 = (V_T \cdot R_H)/(R_3 + R_H)$$

Figure 5:
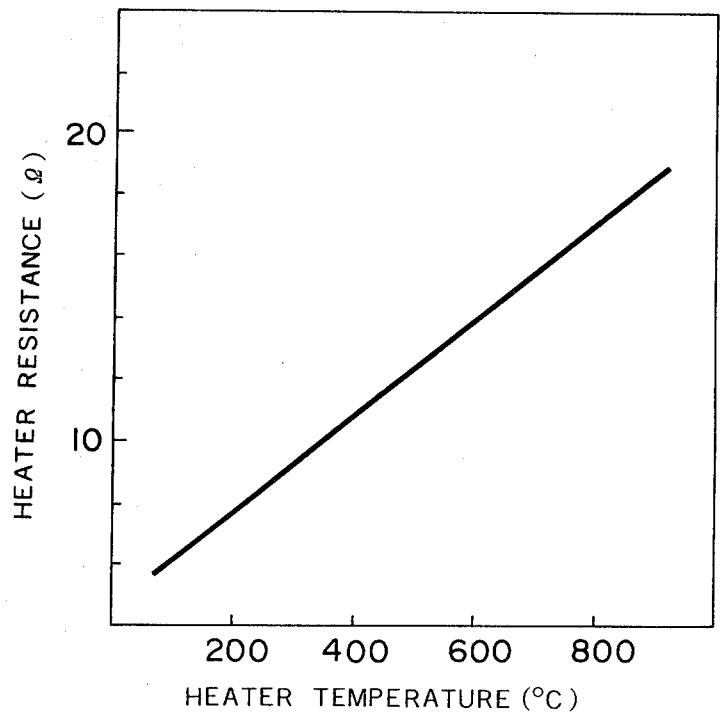
FIG. 5 is a graph showing the relationship between the temperature of the heater in the oxygen sensor element of FIG. 1 and the resistance of this heater.

As is apparent, the potential $E_2$ at the bridge point 52 is the magnitude of a voltage $V_H$ actually applied to the heater $R_H$. The voltage modulating circuit 50 functions such that its output voltage $V_T$ rises when the potential $E_1$ at the bridge point 51 is higher than the potential $E_2$ to allow the heater $R_H$ (14) to generate an increased amount of heat and consequentially to raise its temperature but lowers when the potential $E_1$ is lower then the potential $E_2$ to cause the heater $R_H$ (14) to lower its temperature. Since the resistance $R_H$ of the heater 14 increases in proportion to the temperature of the heater 14, in the manner as shown in FIG. 5 for instance, in the device of FIG. 4 it is intended to maintain the heater 14 at a constant temperature by so regulating the amount of heat the heater 14 generates as to maintain the heater resistance $R_H$ constant. That is, the voltage modulating circuit 50 serves the purpose of maintaining the temperature of the heater 14 constant by controlling the voltage $V_T$ applied to the bridge network so as to render the potential $E_2$ at the bridge point 52 equal to the potential $E_1$ at the bridge point 51 or, in other words, so as to maintain the heater resistance $R_H$ at a constant value given by $(R_2 \cdot R_3)/R_1$.

In the current control part of the device of FIG. 4, the concentration cell part $R_S$ of the oxygen sensor element 10 is connected to a DC power source $V_C$ via a fixed resistance $R_6$ and a transistor 56. There is a voltage divider constituted of two resistances $R_4$ and $R_5$ connected so as to divide the voltage $V_H$ across the heater resistance $R_H$, i.e. the potential $E_2$ at the bridge point 52, and the junction point 53 of this voltage divider is connected to the base of the transistor 56 via a fixed resistance $R_7$ to apply a divided potential $E_3$ at the junction point 53 to the base of the transistor 56.

Figure 6:
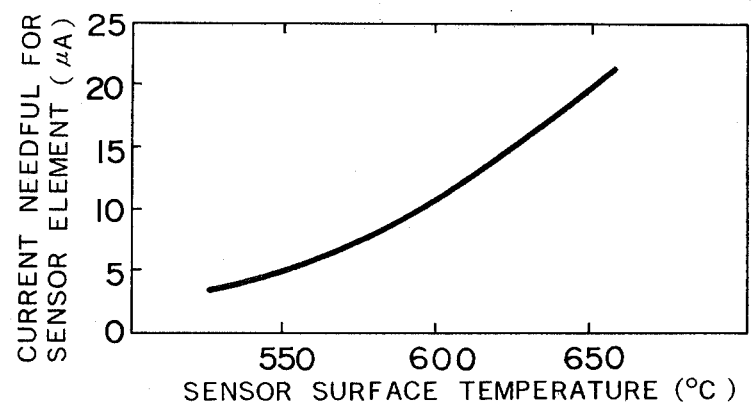
FIG. 6 is a graph showing the relationship between the surface temperature of the oxygen sensor element of FIG. 1 exposed to the exhaust gas of an automotive engine and the intensity of a current to be supplied to the sensitive part of the sensor element to enable it to function properly.

Even though the temperature of the heater 14 is maintained constant in the way as described above, the temperature of the concentration cell part ($R_S$) of the oxygen sensor element 10 is liable to vary by the influence of the temperature of the gas subject to measurement such as the exhaust gas of the automotive engine. Since both the rate of migration of oxygen ions in the solid electrolyte layer 20 and the rate of diffusion of oxygen molecules in the sensor element 10 depend on the temperature, the intensity of the DC current necessary for maintaining a determined level of oxygen partial pressure $P_1$ at the inner electrode layer 18 in the oxygen sensor element 10 varies with temperature of the concentration cell part of the sensor element 10. More particularly, the intensity of the current needs to be increased as the temperature becomes higher in the manner as shown in FIG. 6 by way of example.

Figure 7:
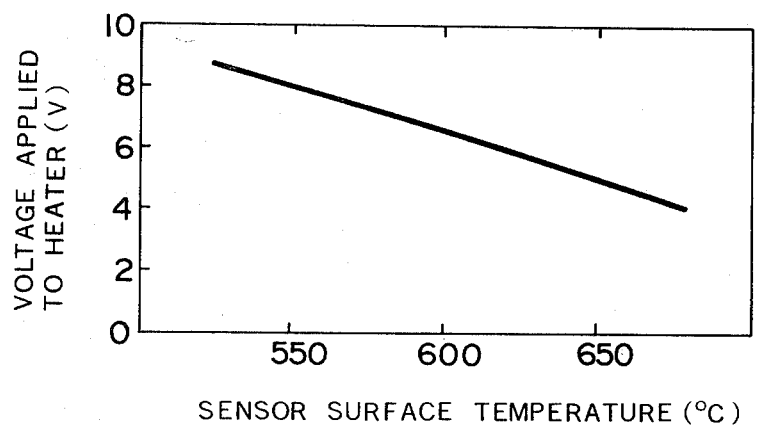
FIG. 7 is a graph showing the relationship between the surface temperature of the oxygen sensor element of FIG. 1 exposed to the exhaust gas and the magnitude of a voltage applied to the heater in the sensor element by the device of FIG. 4.
Figure 8:
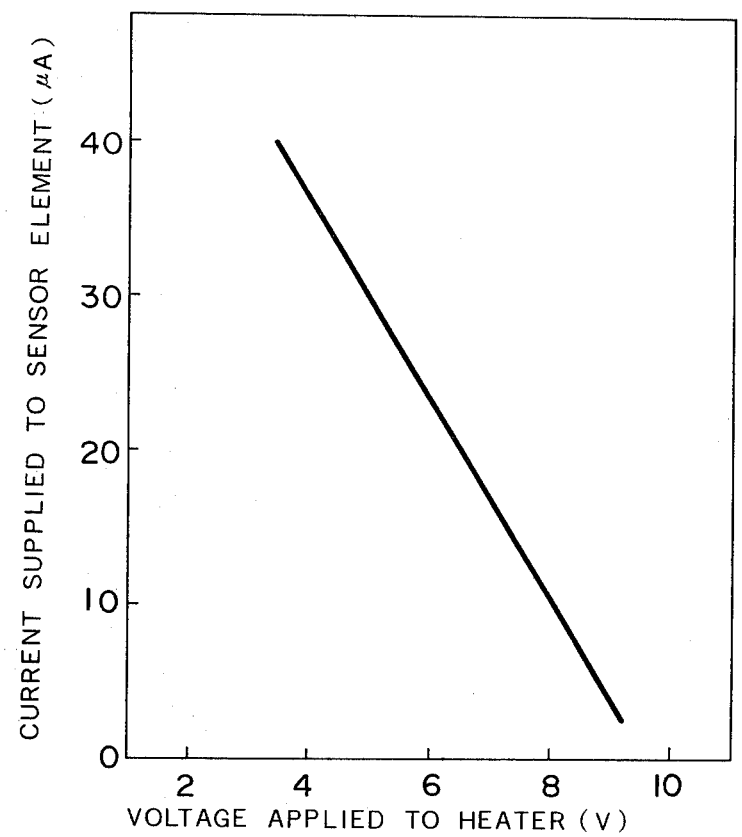
FIG. 8 is a graph showing the relationship between a voltage applied to the heater in the oxygen sensor element of FIG. 1 exposed to the exhaust gas by the device of FIG. 4 and a current supplied from the same device to the sensitive part of the same sensor element.

When the voltage modulating circuit 50 in the device of FIG. 4 functions so as to maintain the heater 14 ($R_H$) in the sensor element 10 at a constant temperature of 700° C., for example, the voltage $V_H$ applied to the heater $R_H$ lowers as the surface temperature of the concentration cell part of the sensor element 10 becomes higher in a relation as shown in FIG. 7. Since the potential $E_3$ obtained by dividing the voltage $V_H$ by the two resistances $R_4$ and $R_5$ is applied to the base of the current-controlling transistor 56, the current $I_C$ being supplied to the concentration cell part $R_S$ of the sensor element 10 increases as the surface temperature of the concentration cell part becomes higher, and vice versa. That is, the current $I_C$ controlled by the device of FIG. 4 varies in inverse proportion to the voltage $V_H$ applied to the heater $R_H$ (14) by the same device, in the manner as shown in FIG. 8 by way of example. Thus, the device of FIG. 4 controls the intensity of the current $I_C$ flowing in the concentration cell part $R_S$ of the sensor element 10 so as to automatically compensate for changes in the temperature of the concentration cell part $R_S$ and, hence, can maintain the oxygen partial pressure at the inner electrode layer 18 in the sensor element 10 at a constant level without influenced by the temperature of the gas subject to measurement.

Figure 9:
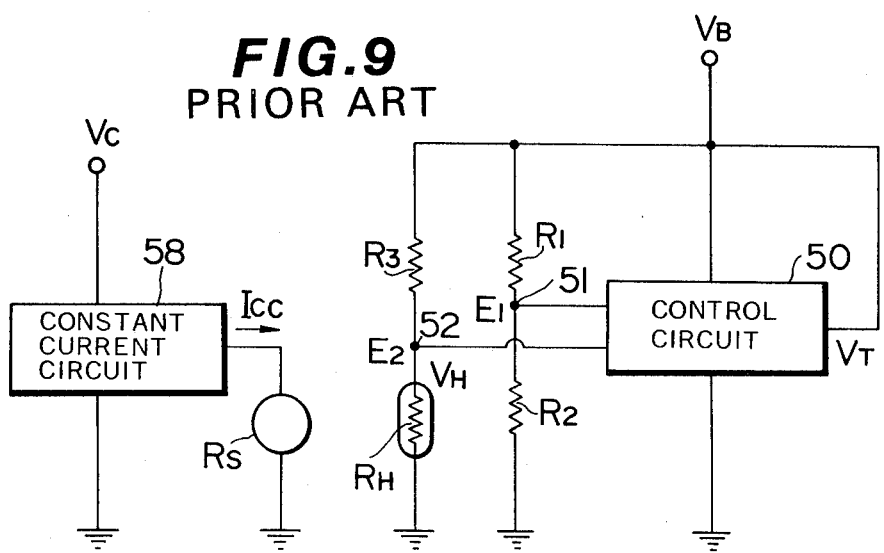
FIG. 9 is a circuit diagram showing a known control device which resembles the device of FIG. 4 but is not in accordance with the present invention.

For comparison, FIG. 9 shows a hitherto employed device for operating the oxygen sensor element 10 of FIG. 1. In this device, voltage $V_H$ applied to the heater resistance $R_H$ is controlled in the same manner as in the device of FIG. 4. In this device, however, a constant current circuit 58 continues to supply a constant DC current $I_{CC}$ to the concentration cell part $R_S$ of the oxygen sensor element 10 regardless of the temperature of the cell part $R_S$ or the magnitude of the voltage $V_H$ applied to the heater $R_H$ (14). That is, the current controlling circuit 58 is completely isolated from the voltage control circuit for the heater $R_H$ (14). Therefore, it is inevitable that the level of the oxygen partial pressure $P_1$ at the inner electrode 18 of the oxygen sensor element 10 fluctuates depending on the temperature of the gas subject to measurement.

What is claimed is:

1. A device for detecting the concentration of oxygen in gases, comprising: p1 an oxygen sensor element comprising:
   a ceramic substrate having a heater in operative combination therewith; and
   a laminate layer comprising a reference electrode layer, an oxygen ion conductive solid electrolyte layer and a measurement electrode layer;
   a power supplying means for applying a variable voltage to said heater in said substrate to maintain the heater at a predetermined temperature by controlling the resistance of said heater at a constant value;
   a current supplying means for supplying a controlled DC current to said laminate to maintain a reference partial pressure at the interface between said reference electrode layer and said solid electrolyte layer; and
   a link means for electrically associating said current supplying means and said power supplying means to transmit a voltage signal representative of said voltage applied to said heater to said current supplying means, said current supplying means functioning to vary the intensity of said current in inverse proportion to the magnitude of said variable voltage applied to said heater.

2. A device according to claim 1, wherein said link means comprises a voltage divider connected to said power supplying means so as to provide said voltage signal as a fraction of said voltage applied to said heater.

3. A device according to claim 2, wherein said current supplying means comprises a current-controlling transistor interposed between a DC power source and said reference electrode layer of said sensor element, said voltage divider being connected to said transistor so as to apply said voltage signal to the base of said transistor.

4. A device according to claim 3, wherein said power supplying means comprises a voltage modulating circuit and three fixed resistors, said heater and said three resistors being connected so as to constitute a bridge network, said voltage modulating circuit being so constructed and arranged as to apply a variable voltage to said bridge network to control the resistance of said heater to a constant value determined by the resistances of said three resistors based on a comparison between a potential at a bridge point between two of said three resistors and a potential at a bridge point between the remaining one of said three resistors and said heater.

5. An oxygen sensor device for the electronic feedback control of the air/fuel ratio of a gas mixture, comprising:
   a casing including mounting means; and
   an oxygen detecting device as claimed in claim 1 and contained within said casing.

* * * * *